United States Patent
Zimmermann et al.

(12)
(10) Patent No.: US 6,950,496 B2
(45) Date of Patent: Sep. 27, 2005

(54) SYSTEM FOR SPECIFYING A SENSOR HOLDER

(76) Inventors: Jürgen Zimmermann, Herrenackerstrasse 14, 64584, Biebesheim (DE); Eriks Blaschka, 7714 Cashel Ct., Charlotte, NC (US) 28270

( * ) Notice: Subject to any disclaimer, the term of this patent is extended or adjusted under 35 U.S.C. 154(b) by 0 days.

(21) Appl. No.: 10/644,990

(22) Filed: Aug. 21, 2003

(65) Prior Publication Data

US 2004/0064027 A1 Apr. 1, 2004

Related U.S. Application Data

(63) Continuation of application No. PCT/DE02/00633, filed on Feb. 21, 2002.

(30) Foreign Application Priority Data

Feb. 21, 2001 (DE) .................................. 101 08 297

(51) Int. Cl.[7] ................................................ H05G 1/60
(52) U.S. Cl. .................... 378/116; 378/191; 378/114
(58) Field of Search .................... 378/191, 114–116, 378/138–140, 119

(56) References Cited

U.S. PATENT DOCUMENTS

| 5,179,579 A | * | 1/1993 | Dove et al. .................... 378/38 |
| 5,195,114 A | | 3/1993 | Sairenji et al. ................ 378/40 |
| 5,513,252 A | | 4/1996 | Blaschka et al. ........... 378/98.8 |
| 6,134,298 A | | 10/2000 | Schick et al. ............... 378/98.8 |
| 6,527,442 B2 | * | 3/2003 | Carroll ......................... 378/189 |
| 6,652,141 B1 | * | 11/2003 | Cianciosi ..................... 378/191 |

FOREIGN PATENT DOCUMENTS

| DE | 33 30 116 A1 | 5/1984 | |
| EP | WO 92/22188 | * 12/1992 | ............ H05G/1/38 |

* cited by examiner

*Primary Examiner*—Craig E. Church
*Assistant Examiner*—Krystyna Suchecki
(74) *Attorney, Agent, or Firm*—Dykema Gossett PLLC (57) ABSTRACT

The invention relates to a system for determining a sensor holder for holding an object, whereby the sensor holder carries a digital sensor of a dental X-ray unit. The inventive system comprises an input and display unit for interactively controlling the same, whereby a schema image can be displayed on the display unit. The system also comprises a processing unit that, based on the selected sensor holder, simulatively generates the schema image from which is apparent which area of the object is displayed when using the selected sensor holder.

23 Claims, 7 Drawing Sheets

SYSTEM FOR SPECIFYING A SENSOR HOLDER

CROSS REFERENCE TO RELATED APPLICATION

This is a continuation of International Application PCT/DE02/00633 filed Feb. 21, 2002, which designated the U.S. All priorities are claimed.

BACKGROUND OF INVENTION a. Field of Invention

The invention relates to a system for specifying a sensor holder for imaging an object, which sensor holder supports a sensor pertaining to digital X-ray apparatus.

b. Description of Related Art

The creation of digital intraoral images using an intraoral sensor is disclosed in EP 0 643 901 (U.S. Pat. No. 5,513,252). The features disclosed in said document are incorporated in this application by reference.

Digital X-ray apparatus, particularly when used in dentistry, exhibits a large number of different sensors and sensor holders. Thus there are various sensor holders, with the aid of which reproducible images can be made, eg, to produce anterior, posterior, bitewing and endo images. It is left to the experience of the user to decide which holder should be used next, for example when creating a series of images. This can be inefficient, since periods of latency cannot be used for preparation.

Furthermore mistakes may be made when a number of sensors are available.

SUMMARY OF INVENTION

It is an object of the present invention to provide a system which makes it a simple matter to select sensor holders and sensors.

This object is achieved by a system showing the features of the independent claims.

The system of the invention for specifying a sensor holder for imaging an object is preferably used in conjunction with digital X-ray apparatus. The sensor holder serves to hold a sensor for digital X-ray apparatus.

The system of the invention has an input device for interactive control of the system. This is preferably a keyboard or a pointing device, such as a mouse.

A display device displays a starting image. This starting image is preferably a panoramic image of a dentition, in particular a dental panoramic radiogram. However, it may conceivably be a standard model of a dentition. This standard model can be selected, if desired, with regard to patient-dependent data. Thus the anatomy of the patient may be taken into account. The user can specify information such as age, size, weight, and skull shape and then select the correct model from a plurality of proposals.

Another component of the present invention is a processing unit which generates, by simulation based on the selected sensor holder, a schematic image, from which it can be seen what area of the object will be imaged when the selected sensor holder is used. In this way it is possible to see, with reference to the panoramic image or the standard model, which area of the dentition will be depicted. The user can thus make a correct selection of sensor holder and sensor.

In order to simplify operation for the user, the area covered by the sensor/sensor holder combination is marked or high-lighted in color. This colored marking is usually laid over the existing model or panoramic image as an overlay.

In order to make the application user-friendly, the system offers a selection of virtual sensors and sensor holders. This overview shows a large number of sensor holders, which are differentiated by colors, symbols, or shapes. These markings correspond to similar or identical markings on the real sensor holders and sensors. It is thus easier for the user to associate the virtual sensor and sensor holder with the real sensor and sensor holder. By showing the characteristic properties of the sensor, such as its size, shape, etc., the risk of confusing sensors is further reduced.

In a preferred embodiment, the selection of the sensor holder is carried out semiautomatically. The user has selection boxes and menus at his disposal, which allow for the selection of a predetermined area of the object. From this area it is possible to draw conclusions concerning the sensor holder which should be selected.

The selection of the holder for creating an image is carried out semiautomatically by specifying a sensor holder with regard to preset assignments (eg, position of the sensor (vertical/horizontal), top or bottom row of teeth, jaw quadrants, only maxillary or only mandibular). If a large number of sensors or sensor holders are offered for selection, it is possible to manually specify that holder which is most suitable for making the intended image.

Another component of the system is a computer interface, via which the selected data are transferred to the X-ray apparatus. The X-ray apparatus can then fully automatically check whether the correct sensor and sensor holder are being used for making the image. Furthermore, the X-ray apparatus can be designed to release from its magazine only those sensors and sensor holders which are intended for use when creating the image.

The system is preferably a known PC controlled by appropriate software. The software realizes the functionality described.

In order to make it possible for the X-ray apparatus to identify the sensor holders and sensors, the latter have identifying means which can be detected mechanically, optically, and/or electrically.

These means comprise optically perceptible color markings or mechanically or optically detectable shapes. Appropriate grooves or reflective surfaces enable mechanical or optical detection. Mechanical identification is also possible by the use of specific cam arrangements. In the case of electrical identification, a large number of possibilities is conceivable. For example, the resistance of the individual assemblies can differ. Furthermore, a chip storing an identification number can be integrated in the sensors or sensor holders.

In order to restrict the possibilities of connecting sensor holder and sensor together, they exhibit special couplings allowing for permissible combinations only.

Another component of the invention is X-ray apparatus equipped with the aforementioned computer interface. In addition, the X-ray apparatus has means for ascertaining the identity of the sensors and sensor holders.

The X-ray apparatus is constructed such that an image will not be created unless the correct combination of sensor holder and sensor is used.

The invention also relates to a method of specifying a sensor holder for imaging an object, which sensor holder supports a digital sensor of dental X-ray apparatus, comprising a first step, in which the sensor holder is selected, a second step, in which the sensor is assigned to a sensor holder, a third step, in which a schematic image is computed based on the position of the selected sensor holder and on the sensor used, from which it can be seen what area of the object will be imaged when the selected sensor holder is used, and a fourth step, in which the schematic image thus generated is displayed and the area covered is optically high-lighted.

Yet another object of the invention is a method of specifying a sensor holder for creating an image of an object, which sensor holder supports a sensor of digital X-ray apparatus, comprising a first step, in which a large number of possible objects to be X-rayed is shown in a general display, a second step, in which a number of objects to be X-rayed is selected from a plurality of objects presented in the general display, and a third step, in which a holder and, optionally, an associated sensor are assigned to each object to be X-rayed.

Advantageously, a fourth step is provided, in which the template is passed, for control purposes, over the general display to reveal the imaging area associated with the template, the third and fourth steps being iteratively continued until a suitable combination of holder and imaging area is displayed.

The object to be X-rayed can advantageously be selected from a general display in the form of a digital X-ray image, preferably an X-ray image of the patient to be examined.

BRIEF DESCRIPTION OF THE DRAWINGS

Below, the invention is explained in greater detail with reference to working examples illustrated diagrammatically in the drawings.

DETAILED DESCRIPTION OF THE PREFERRED EMBODIMENTS

Working example

Figure 1:
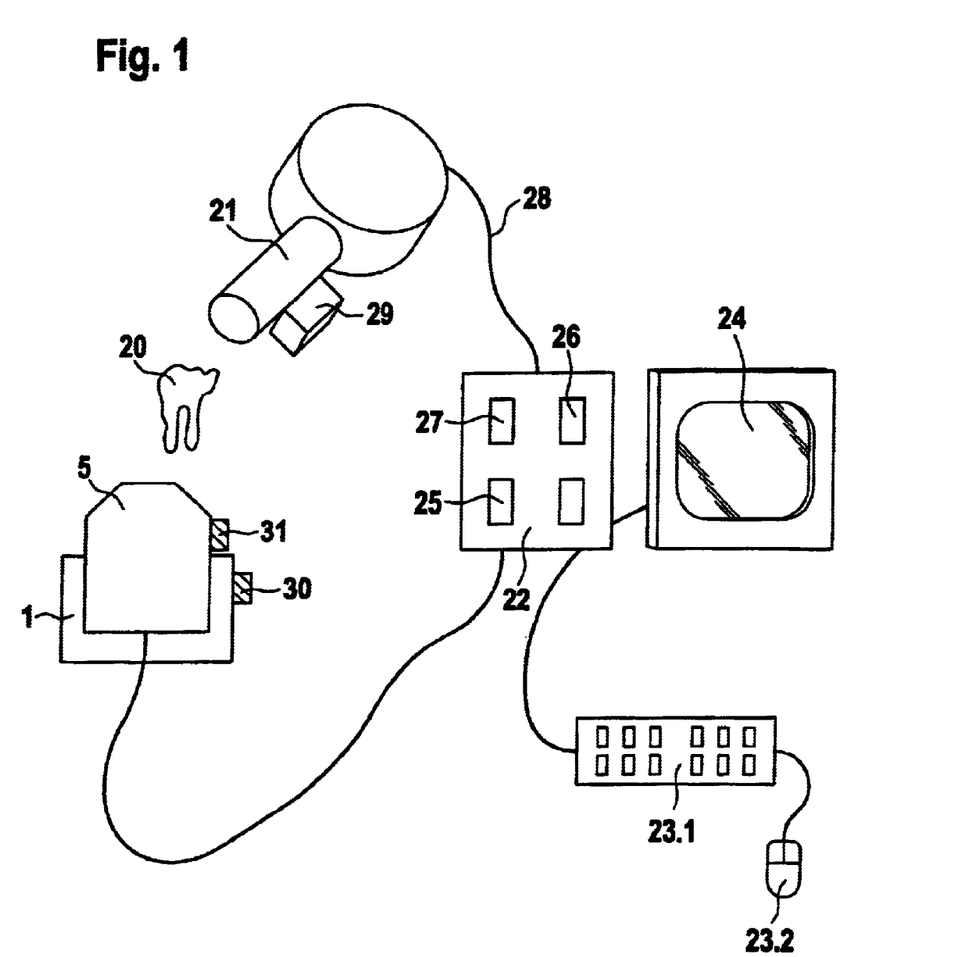
FIG. 1 shows a diagrammatic overview of a system of the invention.

FIG. 1 is a diagrammatic illustration of a system of the invention. In a sensor holder 1 there is held an intraoral sensor 5, with the aid of which the X-ray radiation emitted by an X-ray unit 21 is absorbed after an object 20 to be X-rayed has been radiographed. The sensor holder 1 and the sensor 5 are usually disposed in the oral cavity of a patient.

Furthermore, for selection of the sensor 5 and the sensor holder 1 a processing unit 22 is provided, to which an input device 23.1, 23.2 and also a display unit 24 are connected. The input devices are a keyboard 23.1 and a computer mouse 23.2, and the display unit is a display monitor 24.

In the processing unit 22 there are provided storage areas 25, 26, in which the properties of different sensor holders or sensors are stored which can be addressed by the processing unit 22.

Both the sensor 5 and the X-ray unit 21 can communicate with the processing unit 22, for example, via control cables. Moreover, means 27 may be provided for transferring the selected data relating to the sensor holder to means 29 for detecting identifying means 30, 31 on the sensor holder 1 or sensor 5. This can take place via a connecting cable 28 connected to the X-ray unit 21, on which the detecting means 29 are disposed.

From a plurality of sensor holders 1–4 and a plurality of sensors 5–7 a combination 8 is specified. This combination is optionally placed, with other combinations, in a graphically displayed schematic image 10, cf FIG. 2. The position of the sensor may also be shown in a general display in the form of a tomogram 11, in this case as an outline 8'.

Figure 2:
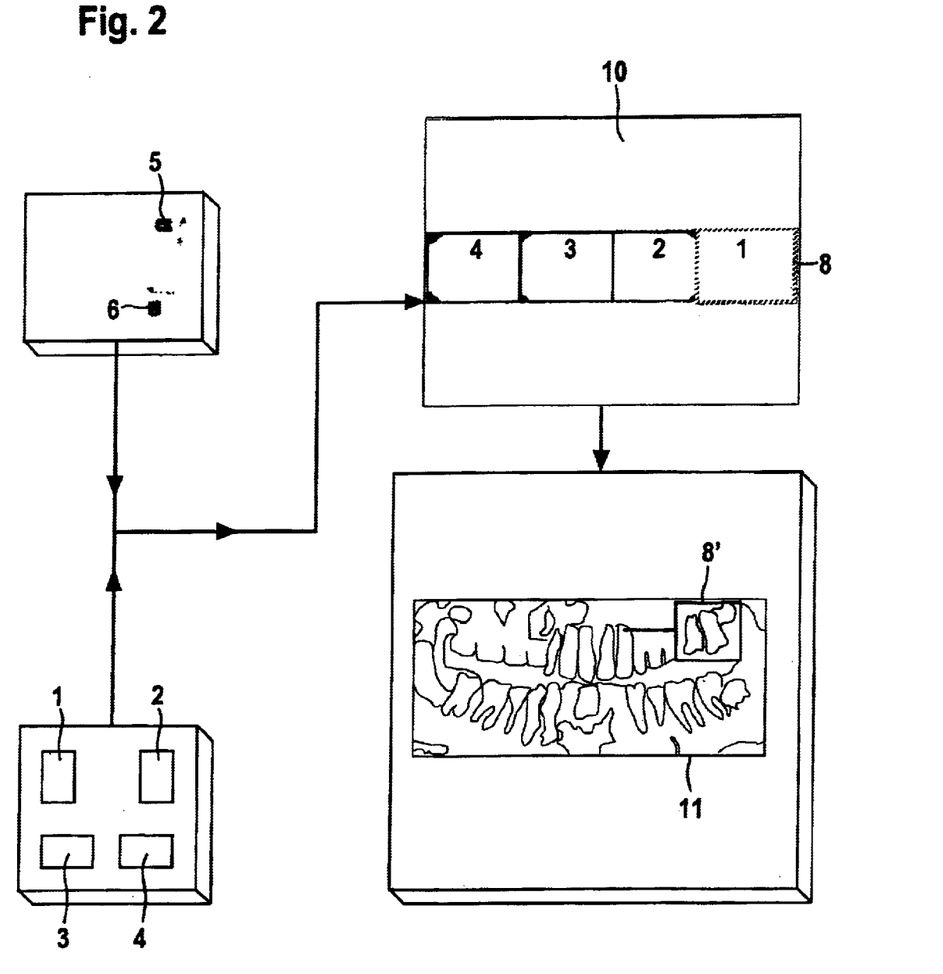
FIG. 2 shows diagrammatically the flow of a method of selecting a sensor holder and sensor for the creation of an X-ray image.

On the basis of this position, a simulated image can be computed with reference to an existing non-patient-dependent general display or, ideally, a patient-related individual X-ray image 11, which simulated image is then displayed. The user can now decide whether the sensor and the corresponding sensor holders should be used for creating a real image. Frequently it is not necessary to display a simulated image, however, and it is sufficient to follow a flowchart shown in the schematic image.

FIGS. 3 to 7 show different schematic images 10 for setting up an X-raying session involving a number of images or for selecting different areas in the image, and also a non-patient-dependent panoramic radiogram 11 as the general display and starting point for the X-ray image to be created. In the panoramic tomogram 11, a number of teeth 12 are displayed high-lighted in the right ramus. These selected teeth 12 represent the actual selection for an X-raying session.

Depending on the schematic image 10, a new X-ray image is always assigned to the currently selected position of the sensor, this being in FIGS. 3 to 7 sensor position 1 in each case.

To each position of the sensor in the schematic image 10 there is assigned a combination 8.1–8.4 of a sensor of a certain size and in a certain position, namely horizontal or vertical, and a corresponding holder, identifiable by a colored display thereof. Of course, it is equally possible to omit the holder entirely at each position of the sensor.

It is at all times possible to deviate from the proposed arrangement of the images by manually specifying imaging sequences by selecting the areas of interest in the X-ray image, whereupon the assignment of a sensor and a holder and also a positioning operation are carried out in the schematic image. This selection is usually carried out by a practitioner. This schematic image 10 can be stored and addressed by the user for creating the image. The user follows the proposed flowchart and possibly makes corrections where necessary due to individual characteristics of the patient.

Figure 3:
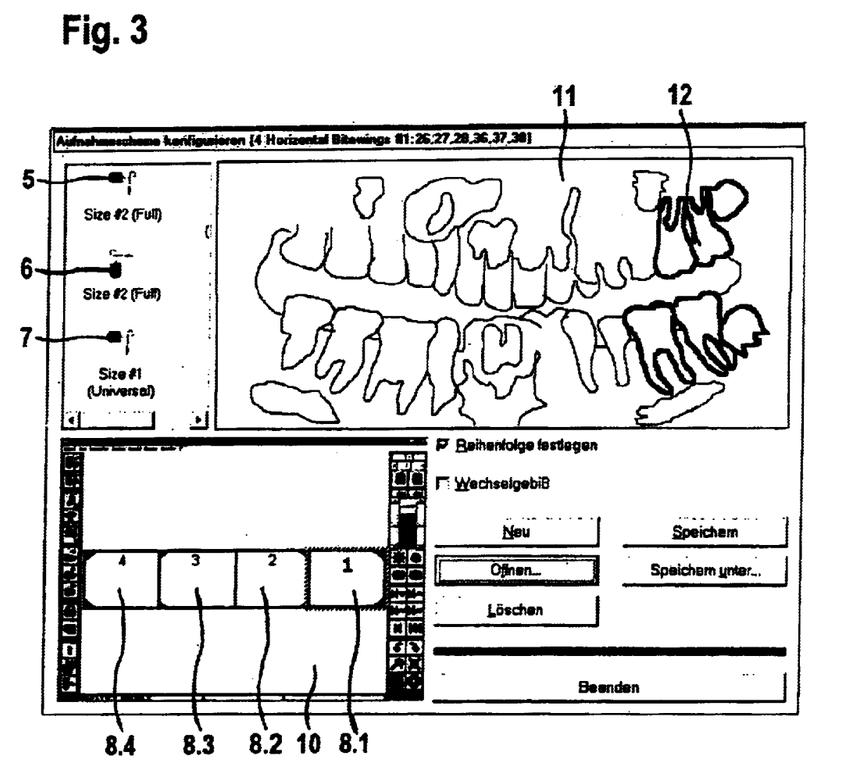
FIGS. 3 to 7 show schematic images for setting up an X-raying session for the creation of a number of images or for selecting different areas in the image.

FIG. 3 shows, in the schematic image 10, an imaging sequence having 4 combinations 8.1 to 8.4, where the currently high-lighted combination 8.1 is planned for X-raying the high-lighted area 12, namely premolars in the right ramus.

Figure 4:
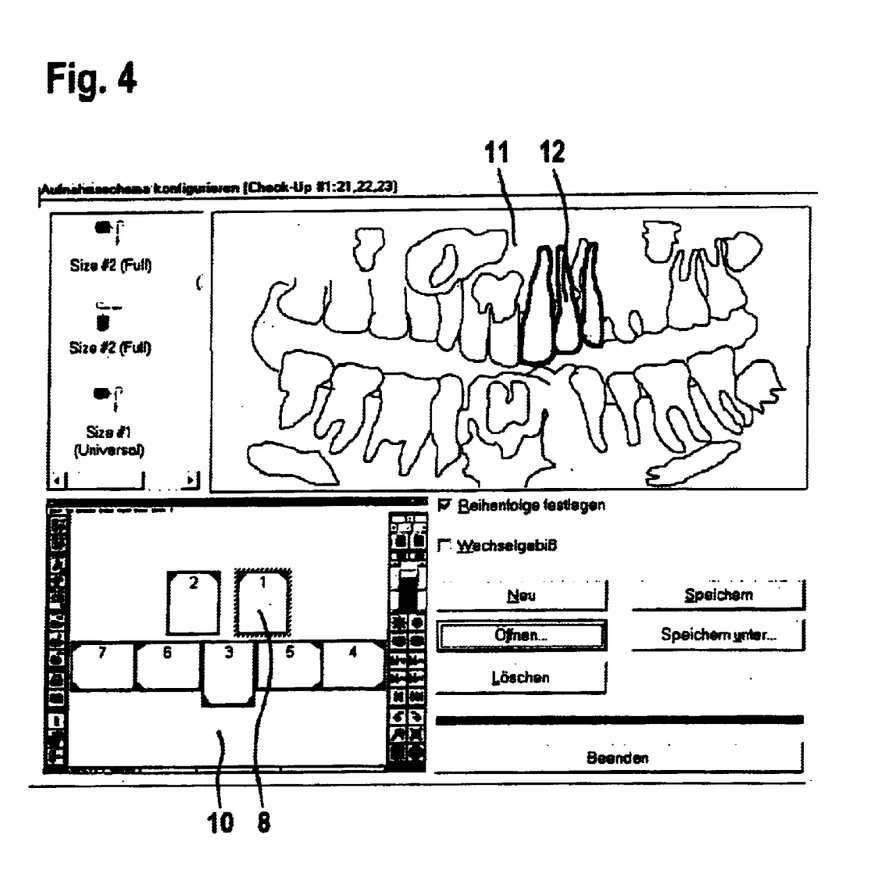

FIG. 4 shows a different arrangement in the schematic image. In this case, the selected combination 8 will create an image in the anterior tooth zone.

Figure 5:
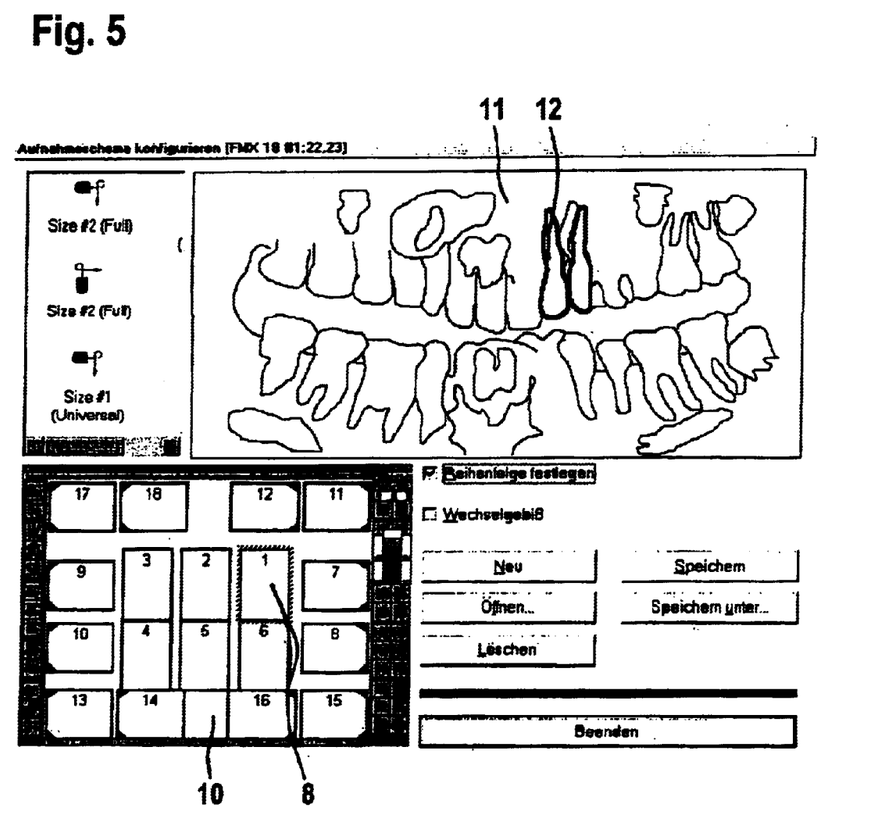

FIG. 5 shows another schematic image 10, in which the selected combination 8 will create an image in the cuspid tooth zone 12 in the upper ramus of the panoramic radiogram 11.

Figure 6:
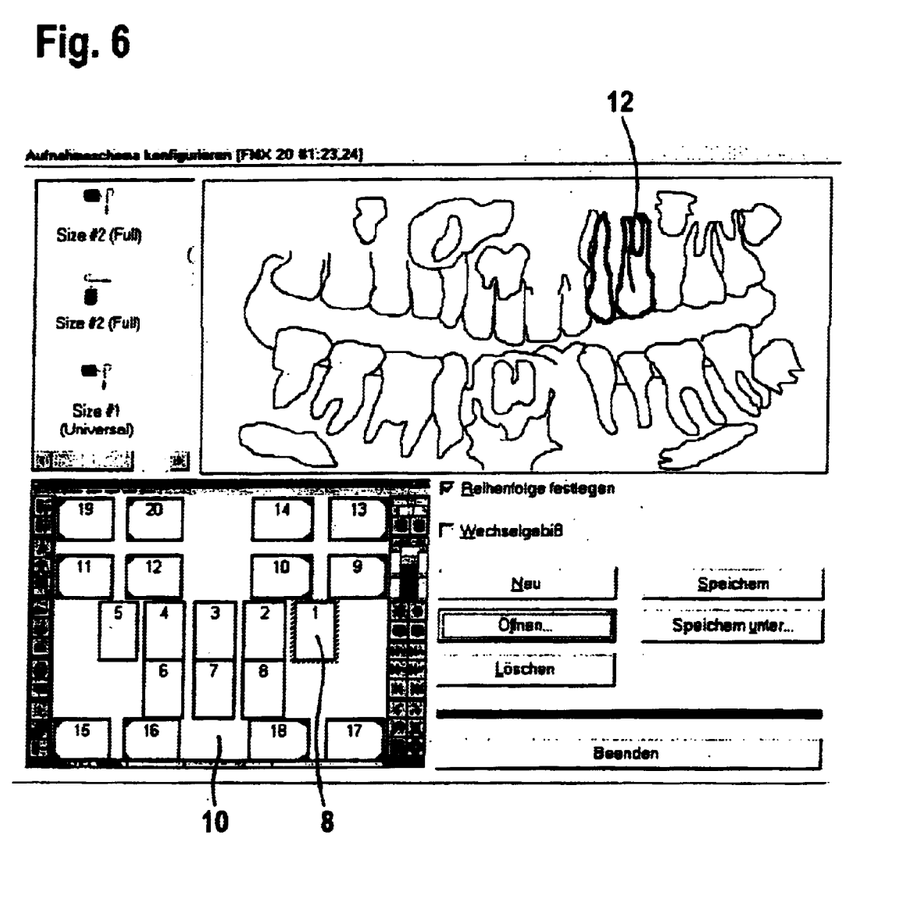

FIG. 6 shows another schematic image 10 presenting a total of 20 combinations 1 to 20 in a special arrangement, in which the selected combination 8 will create an image in a transition region 12 between cuspid and premolar.

Figure 7:
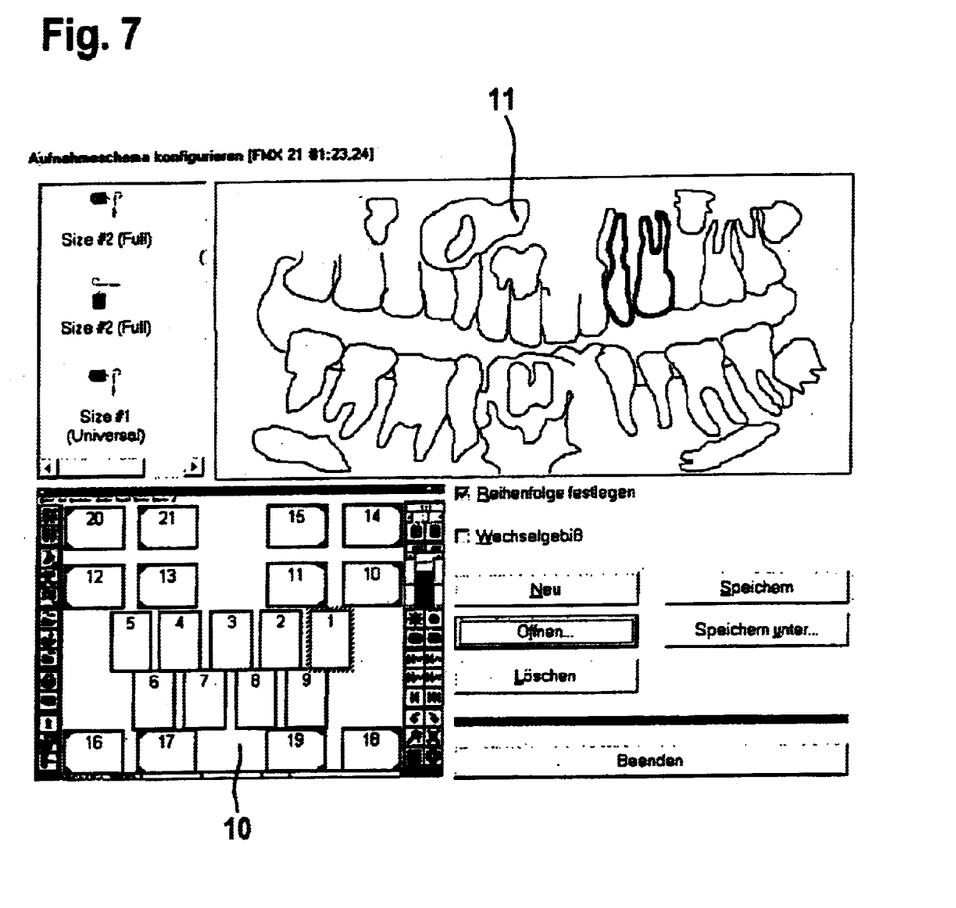

Finally, in FIG. 7 the schematic image 10 has been supplemented by another image, so that a total of 21 combinations are present.

When following the flowchart, the holder and/or sensor necessary for creating the next image is visually clearly indicated so that the user does not himself have to note the optimum order.

Moreover, automatic assignment of the images that have been created to the current position in the flowchart is effected before the next image is made. It is possible to automate this process to such an extent that individual triggering for the creation of each image can be clocked. Alternatively, the next image can be created by special remote instructions sent by the user without him having to directly operate a display and control unit. This makes it possible for the user to stay with the patient.

It is possible to deviate from the method illustrated in FIG. 2 by specifying a combination of sensor and sensor holder by selecting individual areas of interest which are then displayed in the schematic image, so that the schematic image can be generated with reference to the panoramic radiogram. Particularly when the general image used is an individual panoramic radiogram it is possible for the practitioner to optimize the system and imaging sequence The method can be set down in the form of a software program as defined in any one or more of the following method claims. A data medium can contain a data structure that is capable of running on a computer to carry a method as defined in one or more of the following method claims into effect.

What is claimed is:

1. A system for specifying at least one sensor holder for the creation of an image of an object, wherein the sensor holder supports a digital sensor of dental X-ray apparatus, comprising
    an input and display device for interactive control of the system, the display device including a general image displayed containing a predetermined number of possible objects to be X-rayed,
    means for selecting the object to be X-rayed with reference to the general image, and
    a processing unit, in which different sensor holders and, associated sensors are stored in storage areas, and which automatically selects a suitable sensor holder and, an associated sensor on the basis of the desired image of the object and displays the same on the display device.

2. A system as defined in claim 1, wherein the image comprises a digital X-ray image for viewing an area of the object to be imaged when the selected sensor holder is used.

3. A system as defined in claim 2, where the selected area is high-lighted in color.

4. A system as defined in claim 1, wherein a plurality of the sensor holders are provided, the processing unit displaying the plurality of sensor holders, which are differentiated by one of colors, symbols, and shapes.

5. A system as defined in claim 1, wherein the selecting means is effected semiautomatically by the provision of presenting means which permit the selection of a preset area of the object, a storage area being provided for various sensor holders, and comparative means to determine which suitable sensor holders can be specified.

6. A system as defined in claim 1, further comprising means which, following the selection of the sensor holder, transfer the selection data to the X-ray apparatus.

7. A system as defined in claim 1, further comprising a PC controlled by software to realize desired functionality.

8. X-ray apparatus comprising a computer interface for the reception of selected data transmitted by a system as defined in claim 1, wherein the X-ray apparatus has means, for identifying one of the digital sensor and the sensor holder comprising identifying means and for ascertaining whether a selected one of the sensor holder and sensor is used.

9. The X-ray apparatus defined in claim 8, wherein the X-ray apparatus is capable of not creating an image unless the correct combination of the sensor holder and the sensor is used.

10. The X-ray apparatus as defined in claim 9, wherein said means comprise one of optical, electrical, and mechanical sensors.

11. A system for specifying at least one sensor holder for the creation of an image of an object, said sensor holder supporting a digital sensor of a dental X-ray apparatus, comprising
    an input and display device for interactive control of the system, wherein a schematic image of the object to be X-rayed can be displayed on the display device,
    means for selecting one of the sensor holder and the sensor for creating the desired image of the object, and
    a processing unit for automatically generating the schematic image for the selected sensor holder on the basis of the desired image of the object and for displaying said schematic image on the display device,
    wherein a plurality of the sensor holders are provided, the processing unit displaying the plurality of sensor holders, which are differentiated by one of colors, symbols, and shapes.

12. A system as defined in claim 11, wherein the image comprises a digital X-ray image for viewing an area of the object to be imaged when the selected sensor holder is used.

13. A system as defined in claim 12, wherein the selected area is high-lighted in color.

14. A system as defined in claim 11, further comprising a PC controlled by software to realize desired functionality.

15. X-ray apparatus comprising a computer, interface for the reception of selected data transmitted by a system as defined in claim 11, wherein the X-ray apparatus has means for identifying one of the digital sensor and the sensor holder, comprising identifying means and for ascertaining whether a selected one of the sensor holder and sensor is used.

16. The X-ray apparatus defined in claim 15, wherein the X-ray apparatus is capable of not creating an image unless the correct combination of the sensor holder and the sensor is used.

17. The X-ray apparatus as defined in claim 16, wherein said means comprise one of optical, electrical, and mechanical sensors.

18. A system for specifying at least one sensor holder for the creation of an image of an object, said sensor holder supporting a digital sensor of a dental X-ray apparatus, comprising
    an input and display device for interactive control of the system, wherein a schematic image of the object to be X-rayed can be displayed on the display device,
    means for selecting one of the sensor holder and the sensor for creating the desired image of the object, and
    a processing unit for automatically generating the schematic image for the selected sensor holder on the basis of the desired image of the object and for displaying said schematic image on the display device,
    wherein the selecting means is effected semiautomatically by the provision of presenting means which permit the selection of a preset area of the object, a storage area being provided for various sensor holders, and comparative means to determine which suitable sensor holders can be specified.

19. A system for specifying at least one sensor holder for the creation of an image of an object, said sensor holder supporting a digital sensor of a dental X-ray apparatus, comprising
    an input and display device for interactive control of the system, wherein a schematic image of the object to be X-rayed can be displayed on the display device, means for selecting one of the sensor holder and the sensor for creating the desired image of the object, and a processing unit for automatically generating the schematic image for the selected sensor holder on the basis of the desired image of the object and for displaying said schematic image on the display device, further comprising means which, following the selection of the sensor holder, transfer the selection data to the X-ray apparatus.

20. A method of specifying a sensor holder for the creation of an image of an object, wherein the sensor holder supports a digital sensor of dental X-ray apparatus, comprising a first step, in which a predetermined number of possible objects to be X-rayed is displayed in a general display, a second step, in which a predetermined number of objects to be X-rayed is selected from a plurality of objects shown in the general display, and a third step, in which a sensor holder is automatically selected from a plurality of available sensor holders of differing characteristics and an associated sensor is assigned to each of the objects to be X-rayed and a template is shown.

21. A method as defined in claim 20, further comprising a fourth step, in which the template is moved across the general display for purposes of control and thus the imaging area appertaining to the template is revealed, wherein the third and fourth steps are iteratively continued until a suitable combination of holder and imaging area is displayed.

22. A method as defined in claim 20, wherein the general display comprises an X-ray image and, the object to be X-rayed is selected from an X-ray image, of the patient to be examined.

23. A data medium, containing a data structure that is capable of running on a computer for carrying out the method as defined in claim 20 into effect.

* * * * *

UNITED STATES PATENT AND TRADEMARK OFFICE
CERTIFICATE OF CORRECTION

PATENT NO. : 6,950,496 B2
APPLICATION NO. : 10/644990
DATED : September 27, 2005
INVENTOR(S) : J. Zimmermann

It is certified that error appears in the above-identified patent and that said Letters Patent is hereby corrected as shown below:

Title Page, Item (73) Assignee should be as follows:

Sirona Dental Systems GmbH (Bensheim, Germany)

Signed and Sealed this

Twenty-sixth Day of June, 2007

JON W. DUDAS
*Director of the United States Patent and Trademark Office*